US008865624B2

(12) United States Patent
Tanaka et al.

(10) Patent No.: US 8,865,624 B2
(45) Date of Patent: Oct. 21, 2014

(54) INHIBITOR FOR TOBACCO AXILLARY BUD GROWTH AND METHOD FOR INHIBITING TOBACCO AXILLARY BUD GROWTH

(75) Inventors: Motoki Tanaka, Ibaraki (JP); Keijitsu Tanaka, Ibaraki (JP); Takeshi Shibuya, Ibaraki (JP); Eiji Ikuta, Tokyo (JP); Kotaro Yoshinaga, Tokyo (JP); Yuki Yamaguchi, Ibaraki (JP)

(73) Assignee: SDS Biotech K.K., Tokyo (JP)

( * ) Notice: Subject to any disclaimer, the term of this patent is extended or adjusted under 35 U.S.C. 154(b) by 0 days.

(21) Appl. No.: 13/819,540

(22) PCT Filed: Jul. 26, 2011

(86) PCT No.: PCT/JP2011/066934
§ 371 (c)(1),
(2), (4) Date: Feb. 27, 2013

(87) PCT Pub. No.: WO2012/029446
PCT Pub. Date: Mar. 8, 2012

(65) Prior Publication Data
US 2013/0157857 A1 Jun. 20, 2013

(30) Foreign Application Priority Data

Sep. 1, 2010 (WO) .................. PCT/JP2010/064906

(51) Int. Cl.
*A01N 31/02* (2006.01)
*A01N 43/20* (2006.01)
*A01N 37/26* (2006.01)
*A01N 49/00* (2006.01)
*A01N 37/10* (2006.01)
*A01N 43/653* (2006.01)
*A01N 43/713* (2006.01)
*C07C 233/88* (2006.01)
*C07D 333/36* (2006.01)
*C07D 333/32* (2006.01)
*C07D 249/12* (2006.01)
*C07D 257/04* (2006.01)
*C07C 69/88* (2006.01)
*A01N 37/18* (2006.01)
*A01N 37/22* (2006.01)
*A01N 43/10* (2006.01)
*A01N 47/38* (2006.01)

(52) U.S. Cl.
CPC ............ *A01N 43/713* (2013.01); *A01N 43/653* (2013.01); *A01N 43/10* (2013.01); *A01N 43/20* (2013.01); *A01N 47/38* (2013.01); *A01N 31/02* (2013.01); *A01N 37/10* (2013.01); *A01N 37/26* (2013.01); *A01N 37/22* (2013.01); *A01N 49/00* (2013.01)
USPC ........... 504/184; 504/185; 504/186; 504/129; 504/139; 504/149

(58) Field of Classification Search
CPC ....... A01N 31/02; A01N 37/10; A01N 37/18; A01N 37/22; A01N 37/26; A01N 43/10; A01N 43/20; A01N 43/40; A01N 43/78; A01N 43/82; A01N 43/653; A01N 43/713; A01N 47/38; A01N 49/00; C07C 15/04; C07C 15/16; C07C 15/24; C07C 33/02; C07C 69/88; C07C 211/10; C07C 233/88; C07D 211/10; C07D 249/12; C07D 257/04; C07D 277/68; C07D 303/12; C07D 333/20; C07D 333/32; C07D 333/36
USPC .................. 504/184, 185, 186, 129, 139, 149
See application file for complete search history.

(56) References Cited

U.S. PATENT DOCUMENTS

| | | | |
|---|---|---|---|
| 2,923,634 A | 2/1960 | Lindemann | |
| 3,547,620 A | 12/1970 | Olin | |
| 3,672,866 A | 6/1972 | Damiano | |
| 4,046,809 A | 9/1977 | Wilcox | |
| 4,123,250 A | 10/1978 | Kupelian | |
| 4,627,869 A * | 12/1986 | Chang | 504/184 |
| 2005/0233907 A1* | 10/2005 | Nabors et al. | 504/149 |
| 2008/0318781 A1 | 12/2008 | Zagar et al. | |

FOREIGN PATENT DOCUMENTS

| | | |
|---|---|---|
| EP | 2 039 249 A2 | 3/2009 |
| GB | 1 438 312 A | 6/1976 |
| GB | 2 114 566 A | 8/1983 |
| HU | 208224 B | 9/1993 |

(Continued)

OTHER PUBLICATIONS

"Tobacco and Staple Agriculture", 2002, Virginia Places, [online], [retrieved Mar. 27, 2014] Retrieved from the Internet: <URL: http://www.virginiaplaces.org/agriculture/tobaccostaple.html>.*

(Continued)

*Primary Examiner* — Jane C Oswecki
(74) *Attorney, Agent, or Firm* — Sughrue Mion, PLLC

(57) ABSTRACT

The present invention relates to an inhibitor for tobacco axillary bud growth, the inhibitor comprising, as an active ingredient, one or more kinds of very-long chain fatty acid synthesis inhibitors such as a chloroacetamide-based herbicide, fentrazamide, cafenstrole or indanofan; an inhibitor for tobacco axillary bud growth, the inhibitor comprising the aforesaid very-long chain fatty acid synthesis inhibitor together with clorthal-dimethyl or an aliphatic alcohol having 6 to 20 carbon atoms; and a method for inhibiting tobacco axillary bud growth which comprises applying the inhibitor for tobacco axillary bud growth. The inhibitor for tobacco axillary bud growth of the present invention shows sustained drug efficacy at a low concentration, induces neither chemical injury nor disease, and can contribute to the improvement in labor productivity.

13 Claims, No Drawings

(56) References Cited

FOREIGN PATENT DOCUMENTS

| | | |
|---|---|---|
| JP | 61-16395 B2 | 4/1986 |
| JP | 5-19521 B2 | 3/1993 |
| JP | 6-60167 B2 | 8/1994 |
| JP | 2582898 B2 | 2/1997 |
| JP | 2822143 B2 | 11/1998 |
| JP | 2004-359619 A | 12/2004 |
| JP | 2005-529943 A | 10/2005 |
| JP | 2008-127366 A | 6/2008 |
| JP | 2008-524148 A | 7/2008 |
| WO | 2007/014761 A1 | 2/2007 |

OTHER PUBLICATIONS

Chikanori Kawakami et al., "Effect of Amiprofos-methyl on Tobacco Sucker Control", Special bulletin of the Leaf Tobacco Research Laboratory, Jul. 1995, pp. 71-78, No. 5.

J.J. Wheeler et al., "The Mode of Action of Fatty Alcohols on Leaf Tissue", Journal of Plant Growth Regulation, 1991, pp. 129-137, vol. 10, No. 3.

Willard W. Weeks et al., "Effect of Sucker Control on the Volatile Compounds in Flue-Cured Tobacco", Journal of Agriculture and Food Chemistry, Sep. 1986, pp. 899-904, vol. 34, No. 5.

International Search Report for PCT/JP2011/066934 dated Nov. 1, 2011.

* cited by examiner

US 8,865,624 B2

INHIBITOR FOR TOBACCO AXILLARY BUD GROWTH AND METHOD FOR INHIBITING TOBACCO AXILLARY BUD GROWTH

CROSS REFERENCE TO RELATED APPLICATIONS

This application is a National Stage of International Application No. PCT/JP2011/066934 filed Jul. 26, 2011, claiming priority based on International Patent Application No. PCT/JP2010/064906 filed Sep. 1, 2010, the contents of all of which are incorporated herein by reference in their entirety.

TECHNICAL FIELD

The present invention relates to a inhibitor for tobacco axillary bud growth including a specific very-long chain fatty acid synthesis inhibitor as an essential active ingredient and a method for inhibiting tobacco axillary bud growth. More specifically, the present invention relates to: a inhibitor for tobacco axillary bud growth including, as an active ingredient, a very-long chain fatty acid synthesis inhibitor selected from a chloroacetamide-based herbicide, fentrazamide, cafenstrole, and indanofan; a inhibitor for tobacco axillary bud growth including, as active ingredients, the very-long chain fatty acid synthesis inhibitor and chlorthal-dimethyl or an aliphatic alcohol having 6 to 20 carbon atoms, and exhibiting a synergistic effect; and a method for inhibiting tobacco axillary bud growth including applying the inhibitor for tobacco axillary bud growth.

BACKGROUND ART

A labor for removing axillary buds just before harvesting of tobacco is necessary for securing the yield and quality of leaf tobacco. However, in order to perform the labor by hand work, a huge amount of work is required. Therefore, nowadays, a method involving spraying an inhibitor for tobacco axillary bud growth has been developed and widely used.

As an inhibitor for tobacco axillary bud growth which has been widely used from the Showa 30's (1955-1964), there is known a inhibitor including, as an active ingredient, maleic hydrazide or a salt thereof, having a systemic action. The inhibitor is actually used at a concentration as high as about 5,000 ppm and is poor in terms of sustained chemical efficacy. Hence, there has been a problem in that a large amount of the inhibitor is required. Further, hydrazine produced by decomposition of maleic hydrazide exhibits oncogenic potential, and hence use of the inhibitor is currently restricted.

Therefore, in recent years, a contact-type inhibitor for tobacco axillary bud growth, which is sprayed by contact with stem, has been used. As the contact-type inhibitor, there are known, for example, an inhibitor including a saturated aliphatic alcohol as an active ingredient and an inhibitor including a dinitroaniline-based chemical substance as an active ingredient.

The inhibitor for axillary bud growth including a saturated aliphatic alcohol as an active ingredient has a high effect of killing axillary buds by contact. However, the inhibitor including a saturated aliphatic alcohol as an active ingredient is poor in terms of sustained chemical efficacy and requires spraying of the inhibitor at least twice in order to prevent elongation of axillary buds in the later growth period. In addition, attachment of the sprayed inhibitor to leaves at the time of use causes bleaching, another harmful effect of the inhibitor, and reduction in quality of the leaves. Further, as the inhibitor is dropped and accumulated at the base part of a plant, all stem bases are necrotized, resulting in killing the plant.

On the other hand, the inhibitor including a dinitroaniline-based chemical substance as an active ingredient is disclosed in, for example, U.S. Pat. No. 3,672,866 (Patent Document 1), U.S. Pat. No. 4,046,809 (Patent Document 2) and U.S. Pat. No. 4,123,250 (Patent Document 3). The inhibitor including a dinitroaniline-based compound as an active ingredient contains a certain organic solvent. The inhibitor has an effect of stopping growth of axillary buds by dehydrating and necrotizing axillary buds by contact of the dinitroaniline-based chemical substance and the organic solvent with the axillary buds and allowing the above-mentioned chemical substance to be absorbed from the axillary bud plumule part or from wounds after removal of the axillary buds to inhibit cell division and has a high effect of inhibiting formation and elongation of axillary buds.

However, the inhibitor including a dinitroaniline-based chemical substance as an active ingredient has the following problems, for example. The inhibitor sometimes causes harmful effects such as deformation of young leaves of the upper node, lack in expansion, necrosis of mesophyll, damages of the petiole parts of middle or upper leaves, developmental disorders of adventitious roots, and necrosis immediately after spraying; and induces diseases such as hollow heart, crown rot, and gray mold from wound sites formed in the petiole base by the harmful effects to cause adverse effects on the yield and quality of leaf tobacco.

U.S. Pat. No. 2,923,634 (Patent Document 4) describes that chlorthal-dimethyl is used as an herbicide. Further, JP 05-19521 B (Patent Document 5, U.S. Pat. No. 4,627,869) describes that chlorthal-dimethyl is used as an inhibitor for tobacco axillary bud growth.

However, the inhibitor for tobacco axillary bud growth including chlorthal-dimethyl as an active ingredient and described in Patent Document 5 is actually used at a concentration as extremely high as 1% or more and is poor in terms of sustained chemical efficacy. Therefore, it is necessary to use the inhibitor repeatedly until harvest, and hence there is a problem in that a large amount of the inhibitor is required.

As mentioned above, the inhibitor for axillary bud growth currently used in cultivation of tobacco have many problems yet to be solved from the viewpoint of sustainment of the chemical efficacy and occurrence of harmful effects.

Therefore, an inhibitor for tobacco axillary bud growth which is excellent in terms of sustained chemical efficacy, induces no harmful effect and no disease, and can contribute to improvement in labor productivity has been desired.

A very-long chain fatty acid synthesis inhibitor to be used in the present invention is a known compound, and for example, JP 61-16395 B (Patent Document 6, U.S. Pat. No. 4,802,907), GB 1438312 A (Patent Document 7), U.S. Pat. No. 3,547,620 (Patent Document 8), GB 2114566 A (Patent Document 9), JP 06-60167 B (Patent Document 10, U.S. Pat. No. 5,147,445), JP 2582898 B2 (Patent Document 11, U.S. Pat. No. 5,076,830), JP 2822143 B2 (Patent Document 12, U.S. Pat. No. 5,362,704), HU 208224 B (Patent Document 13), JP 2004-359619A (Patent Document 14), JP 2005-529943 W (Patent Document 15, WO 2003/105587), and JP 2008-524148 W (Patent Document 16, WO 2006/063835) describe that thenylchlor, metolachlor, alachlor, dimethenamid, cafenstrole, indanofan, fentrazamide, and propisochlor are used as herbicides, respectively. Hitherto, however, the very-long chain fatty acid synthesis inhibitor has not been used as an inhibitor for tobacco axillary bud growth.

CITATION LIST

Patent Document

[PATENT DOCUMENT 1] U.S. Pat. No. 3,672,866
[PATENT DOCUMENT 2] U.S. Pat. No. 4,046,809
[PATENT DOCUMENT 3] U.S. Pat. No. 4,123,250
[PATENT DOCUMENT 4] U.S. Pat. No. 2,923,634
[PATENT DOCUMENT 5] JP 05-19521 B
[PATENT DOCUMENT 6] JP 61-16395 B
[PATENT DOCUMENT 7] GB 1438312 A
[PATENT DOCUMENT 8] U.S. Pat. No. 3,547,620
[PATENT DOCUMENT 9] GB 2114566 A
[PATENT DOCUMENT 10] JP 06-60167 B
[PATENT DOCUMENT 11] JP 2582898 B2
[PATENT DOCUMENT 12] JP 2822143 B2
[PATENT DOCUMENT 13] HU 208224 B
[PATENT DOCUMENT 14] JP 2004-359619 A
[PATENT DOCUMENT 15] JP 2005-529943 W
[PATENT DOCUMENT 16] JP 2008-524148 W

SUMMARY OF INVENTION

Technical Problem

An object of the present invention is to provide an inhibitor for tobacco axillary bud growth, which shows sustained chemical efficacy at a low concentration, induces no harmful effect and no disease, and can contribute to improvement in labor productivity.

Solution to Problem

The inventors of the present invention have made various studies on many kinds of compounds to develop a novel inhibitor for tobacco axillary bud growth. As a result, the inventors have found that a very-long chain fatty acid synthesis inhibitor can suppress growth of tobacco axillary buds at a low concentration for a long period of time and has no harmful effect on stem and leaf parts of tobacco.

The inventors have further found that, when the very-long chain fatty acid synthesis inhibitor is used in combination with chlorthal-dimethyl or an aliphatic alcohol having 6 to 20 carbon atoms, the effect of inhibiting growth of tobacco axillary buds can be improved synergistically, thus completing the present invention.

The very-long chain fatty acid synthesis inhibitor to be used in the present invention is known as an herbicide, but there is no literature describing use of the synthesis inhibitor as an inhibitor for tobacco axillary bud growth.

The present invention relates to the following inhibitor for tobacco axillary bud growth and method for inhibiting tobacco axillary bud growth.

(1) An inhibitor for tobacco axillary bud growth, including, as an active ingredient, one or more kinds selected from very-long chain fatty acid synthesis inhibitors.

(2) The inhibitor for tobacco axillary bud growth according to (1) above, in which the very-long chain fatty acid synthesis inhibitors include one or more kinds selected from the group consisting of a chloroacetamide-based herbicide, fentrazamide, cafenstrole and indanofan.

(3) The inhibitor for tobacco axillary bud growth according to (2) above, in which the chloroacetamide-based herbicide is thenylchlor, metolachlor, alachlor, dimethenamid, butachlor, pretilachlor or propisochlor.

(4) The inhibitor for tobacco axillary bud growth according to any one of (1) to (3) above, further including chlorthal-dimethyl.

(5) The inhibitor for tobacco axillary bud growth according to (4) above, including cafenstrole or thenylchlor; and chlorthal-dimethyl.

(6) The inhibitor for tobacco axillary bud growth according to any one of (1) to (3) above, further including an aliphatic alcohol having 6 to 20 carbon atoms.

(7) The inhibitor for tobacco axillary bud growth according to (6) above, in which the aliphatic alcohol having 6 to 20 carbon atoms is decyl alcohol, 2-ethyl hexanol or geraniol.

(8) A method for inhibiting tobacco axillary bud growth, including applying the inhibitor for tobacco axillary bud growth according to any one of (1) to (7) above.

Effects of Invention

The inhibitor for tobacco axillary bud growth of the present invention has a high effect of inhibiting axillary bud growth and shows sustained chemical efficacy. Further, the inhibitor has no harmful effects on the stem and leaf parts and the root part. Therefore, in cultivation of tobacco, the inhibitor can achieve an increase in yield, improvement of quality, and improvement of labor productivity by reduction in labor for removing axillary buds.

DESCRIPTION OF EMBODIMENTS

Examples of a very-long chain fatty acid synthesis inhibitor to be used in the present invention include a chloroacetamide-based compound, an oxyacetamide-based compound, and an alkanamide-based compound.

Specific examples of the chloroacetamide-based compound include acetochlor, alachlor, allidochlor, xylachlor, diethatyl-ethyl, dimethachlor, dimethenamid, dimethenamid-P, thenylchlor, delachlor, terbuchlor, butachlor, butenachlor, prynachlor, pretilachlor, propachlor, pethoxamid, metazachlor, metolachlor, S-metolachlor and propisochlor.

Specific examples of the oxyacetamide-based compound include flufenacet and mefenacet.

Examples of the alkanamide-based compound include diphenamid, naproanilide and napropamide.

Examples of the very-long chain fatty acid synthesis inhibitor except the foregoing include fentrazamide, cafenstrole, anilofos, piperophos, indanofan, ipfencarbazone, tridiphane and epronaz.

In consideration of an effect of inhibiting formation and growth of tobacco axillary buds, the chloroacetamide-based compound is particularly desirably thenylchlor, metolachlor, alachlor, dimethenamid, butachlor, pretilachlor or propisochlor, and the very-long chain fatty acid synthesis inhibitor except the foregoing is particularly desirably fentrazamide, cafenstrole or indanofan.

In the case of treating tobacco with the inhibitor for tobacco axillary bud growth of the present invention including, as an active ingredient, the very-long chain fatty acid synthesis inhibitor alone, it is recommended that the concentration of the very-long chain fatty acid synthesis inhibitor be 0.05 to 0.5% by mass.

Further, when the very-long chain fatty acid synthesis inhibitor is used in combination with chlorthal-dimethyl or an aliphatic alcohol having 6 to 20 carbon atoms, it is possible to synergistically improve an effect of inhibiting growth of tobacco axillary buds and sustainment of the effect.

When used in combination with chlorthal-dimethyl, the very-long chain fatty acid synthesis inhibitor is preferably thenylchlor or cafenstrole from the standpoint of the effect of inhibiting growth of tobacco axillary buds.

It should be noted that the inhibitor for tobacco axillary bud growth of the present invention including chlorthal-dimethyl and the very-long chain fatty acid synthesis inhibitor in combination encompasses an embodiment of an inhibitor formed by separately formulating chlorthal-dimethyl and the very-long chain fatty acid synthesis inhibitor and appropriately mixing them before use.

In the case of treating tobacco with the inhibitor for tobacco axillary bud growth of the present invention including the very-long chain fatty acid synthesis inhibitor and chlorthal-dimethyl in combination, it is recommended that the concentration of one or more kinds of active ingredients selected from the above-mentioned very-long chain fatty acid synthesis inhibitors be 0.0001% to 0.1% by mass, and the concentration of chlorthal-dimethyl be 0.001 to 3% by mass.

The mixing ratio of the very-long chain fatty acid synthesis inhibitor to chlorthal-dimethyl is not particularly limited and is selected from a wide range depending on the combination of the selected very-long chain fatty acid synthesis inhibitor. The mixing ratio is desirably 1:1,000 to 1,000:1, more desirably 1:300 to 300:1 in terms of mass ratio.

Examples of the aliphatic alcohol having 6 to 20 carbon atoms to be used in the present invention include acetone glyceryl acetal, ambrinol, α-bisabolol, d-borneol, l-borneol, 2-butoxyethanol, α-campholenol, l-carveol, carveol, β-caryophyllene alcohol, cedrenol, cedrol, citral, citronellal, citronellol, l-citronellol, cyclohexanol, 2-cyclohexylethanol, 2,4-decadienol, 3-decanol, decyl alcohol, 2-decenol, 9-decenol, 4-decenol, dihydrocarveol, 7,8-dihydro-β-ionol, 3,7-dimethyl-6-octen-3-ol, dihydromyrcenol, dihydroperillyl alcohol, 2,5-dimethyl-1,4-dithiane-2,5-diol, 2,6-dimethyl-4-heptanol, 3,7-dimethyl-1,5,7-octatrien-3-ol, 2,6-dimethyl-2-heptanol, 3,6-dimethyl-3-octanol, 2,4-dimethyl-4-nonanol, 2-dodecanol, dodecanol, 2-dodecenol, elemol, 2-ethylbutanol, 2-ethylfenchol, 2-ethylhexanol, farnesol, fenchyl alcohol, geraniol, geranyllinalool, heptadecanol, heptanal glyceryl acetal, 2-heptanol, 3-heptanol, 4-heptanol, heptanol, 1-hepten-3-ol, 2-heptenol, 3-heptenol, cis-4-heptenol, hexadecanol, 2,4-hexadienol, hexanal glyceryl acetal, hexanol, 2-hexanol, 3-hexanol, 4-hexanol, 1-hexen-3-ol, trans-2-hexenal glyceryl acetal, 2-hexenol, 3-hexenol, cis-2-hexenol, cis-3-hexenol, cis-4-hexenol, trans-2-hexenol, trans-3-hexenol, trans-4-hexenol, hydroxycitronellal diethyl acetal, hydroxycitronellol, α-ionol, β-ionol, isoborneol, isodihydrocarveol, isogeraniol, isophytol, isopulegol, isovaleraldehyde glyceryl acetal, lavandulol, 8-p-menthene-1,2-diol, linalool, linanool oxide, 2-p-menthene-1,2-diol, 2,8-p-menthadiene-1-ol, 1,8-p-menthadiene-4-ol, menthadienol, p-menthan-2-ol, p-menthan-7-ol, p-menthan-8-ol, 8-p-menthan-7-ol, 1-menthol, dl-menthol, 3-(menthoxy)-1,2-propanediol, 3-methyl-2-pentanol, 4-methyl-2-pentanol, 6-methyl-3-heptanol, 5-methyl-3-heptanol, 2-methyl-3-hexanol, 3-methyl-3-pentanol, 6-methyl-5-hepten-2-ol, 2-methyl-5-hepten-2-ol, 5-methylhexanol, 2-methylpentanol, 3-methylpentanol, 4-methylpentanol, 3-(methylthio)hexanol, myrcenol, myrtenol, neodihydrocarveol, α-neomenthol, neomenthol, nerol, cis-nerolidol, trans-nerolidol, nerolidol, 2,4-nonadienol, 3,6-nonadienol, trans, cis-2,6-nonadienol, nonadienol, nonanol, 2-nonanol, 3-nonanol, 1-nonen-3-ol, 3-nonenol, 6-nonenol, cis-2-nonenol, trans-2-nonenol, 2,6-dimethyl-5,7-octadien-2-ol, 1,5-octadien-3-ol, octadecanol, 3,5-octadienol, 1,3-octanediol, 2-octanol, 3-octanol, octanol, 1-octen-3-ol, 2-octen-4-ol, 2-octenol, 3-octenol, cis-5-octenol, cis-9-octadecenol, pentadecanol, perillyl alcohol, phytol, pinocarveol, piperitol, rhodinol, α-santalol, sclareol, terpineol, 1-terpineol, 4-terpineol, α-terpineol, β-terpineol, 4-tert-butylcyclohexanol, tetradecanol, tetrahydrocuminol, 3,7-dimethyloctanol, 3,7-dimethyl-2-octanol, 2,6-dimethyl-2-octanol, 3-thujanol, sabinene hydrate, tridecanol, 2-tridecenol, 3,3,5-trimethylcyclohexanol, 3,5,5-trimethylhexanol, 2,4-undecadienol, 2-undecanol, undecanol, cis,cis-1,5,8-undecatrien-3-ol, 10-undecenol, 2-undecenol, verbenol, vetiverol, viridiflorol, 3-l-menthoxy-2-methylpropane-1,2-diol, citral glyceryl acetal, menthone 1,2,-glyceryl acetal, 1-p-menthen-9-ol, 1,2-dihydrolimonen-10-ol, 2,3,4-trimethyl-3-pentanol, 2,4-dimethylcyclohexylmethanol, 2-methyl-1-hepten-3-ol, 2-tert-butylcyclohexanol, 3-ethyl-3-octanol, 4-isopropylcyclohexanol, 5-hexenol, 5-octene-1,3-diol, 6-hydroxydihydrotheaspirane, 8-ethyl-1,5-dimethylbicyclo[3.2.1]octan-8-ol, cis-3-heptenol, cis-4-octenol, cyclododecanol, u-limonene-10-ol, d-trans,cis-1(7),8-p-menthadien-2-ol, 3,7-dimethyl-1,6-nonadien-3-ol, linalool oxide (pyranoid), quercivorol, nerolidol oxide, nootkatol, p-menthan-3,8-diol, santalol, and tetrahydronootkatol.

In consideration of issues such as compatibility with the very-long chain fatty acid synthesis inhibitor, the aliphatic alcohol having 6 to 20 carbon atoms is particularly desirably decyl alcohol, 2-ethylhexanol or geraniol.

The mixing ratio of the very-long chain fatty acid synthesis inhibitor to the aliphatic alcohol having 6 to 20 carbon atoms is not particularly limited and is selected from a wide range depending on the combination of the selected very-long chain fatty acid synthesis inhibitor and the aliphatic alcohol.

It should be noted that the inhibitor for tobacco axillary bud growth of the present invention including, as active ingredients, the very-long chain fatty acid synthesis inhibitor and the aliphatic alcohol having 6 to 20 carbon atoms in combination encompasses an embodiment of an inhibitor formed by separately formulating both the components and appropriately mixing them before use.

In the case of treating tobacco with the inhibitor for tobacco axillary bud growth of the present invention including the very-long chain fatty acid synthesis inhibitor and the aliphatic alcohol having 6 to 20 carbon atoms in combination, it is recommended that the concentration of one or more kinds of active ingredients selected from the above-mentioned very-long chain fatty acid synthesis inhibitors be 0.01 to 0.3% by mass.

In addition, in the case of using the very-long chain fatty acid synthesis inhibitor and the aliphatic alcohol having 6 to 20 carbon atoms in combination, the mixing ratio of one or more kinds of active ingredients selected from the above-mentioned very-long chain fatty acid synthesis inhibitors to the aliphatic alcohol having 6 to 20 carbon atoms is usually 1:1,000 to 1,000:1, preferably 1:300 to 300:1 in terms of mass ratio.

Although the inhibitor for tobacco axillary bud growth of the present invention may be used without adding any other components, the inhibitor is usually mixed with a solid carrier, a liquid carrier or a gas carrier, and as necessary, is further supplemented with a surfactant, an extender, a colorant, a binder, an antifreezing agent, an ultraviolet absorber, or the like, to be formulated into an oil solution, an emulsion, a solubilizer, a wettable powder, a suspension, a flowable agent, a powder, or the like before application.

The surfactant is not particularly limited, and examples thereof include a phenylphenolsulfonic acid-formaldehyde condensate, sodium dioctyl sulfosuccinate, a sodium alkyl-naphthalene sulfonate, a polyoxyethylene alkyl phenyl ether, a sodium naphthalenesulfonate condensate, a sodium polyoxyethylene alkyl phenyl ether sulfoacetate, a ammonium polyoxyethylene alkyl phenyl ether sulfate, an ethylene oxide-propylene oxide copolymer, and an alkenyl sulfonate.

The extender is not particularly limited, and examples thereof include: plant powders such as soybean powder, tobacco powder, wheat powder, and wood powder; clay minerals such as clay, bentonite, acid clay, and radiolite; talcs such as talc powder and agalmatolite powder; mineral powders such as diatomaceous earth and mica powder; and sodium bicarbonate, calcium carbonate, alumina, and activated carbon.

The colorant is not particularly limited, and examples thereof include: inorganic pigments such as iron oxide, titanium oxide, and Prussian blue; organic dyes such as an alizarin dye, an azo dye, and a metallophthalocyanine dye; and trace elements such as iron, manganese, boron, copper, cobalt, molybdenum, and zinc.

The binder is not particularly limited, and examples thereof include carboxymethylcellulose sodium salt, starch, sodium lignin sulfonate, dextrin and polyvinyl alcohol.

The antifreezing agent is not particularly limited, and examples thereof include glycerin, ethylene glycol, and propylene glycol.

The ultraviolet absorber is not particularly limited, and examples thereof include substituted benzophenone, a diphenylacrylonitrile ester and a cinnamic acid ester.

As a tobacco (*Nicotiana tabacum*) cultivar which is suppressed by the inhibitor for tobacco axillary bud growth of the present invention in formation and elongation of axillary buds, there are given for example: domestic cultivars typified by Matsukawa, Daruma, Awa, and Siroenshu; flue-cured cultivars typified by Coker 319, Virginia 115, MC 1, Okinawa 2, Bright Yellow 4, Tsukuba 1, and Tsukuba 2; and burley cultivars typified by Burley 21, Kitakami 1, Michinoku 1 and Michinoku 2.

The use amount of the inhibitor for tobacco axillary bud growth of the present invention varies depending on the cultivar, method and timing of use, and the use amount of a spray solution per plant is desirably 5 to 40 ml, more desirably 15 to 30 ml.

In addition, with regard to the number of times of application of the inhibitor for tobacco axillary bud growth of the present invention, in the case where the first application is carried out before blooming of tobacco or before top pruning or in the case where tree vigor of tobacco is strong even after the first spraying after the top pruning, the inhibitor is effectively applied by performing the first application and subsequently the second spraying two weeks after the first application in the same manner as in the first application.

The inhibitor for tobacco auxiliary bud growth of the present invention may further contain known herbicides in order to enhance the efficacy. Examples of the herbicides include the following: ioxynil, aclonifen, aziprotryne, acifluorfen-sodium, azimsulfuron, asulam, atrazine, azafenidin, amicarbazone, amidosulfuron, amitrole, aminocyclopyrachlor, aminopyralid, amiprophos-methyl, ametryne, alloxydim, isouron, isoxachlortole, isoxaflutole, isoxaben, isoproturon, imazaquin, imazapic, imazapyr, imazamethabenz-methyl, imazamox-ammonium, imazethapyr, imazosulfuron, indaziflam, eglinazine-ethyl, esprocarb, ethalfluralin, ethametsulfuron-methyl, ethidimuron, ethoxysulfuron, ethoxyfen-ethyl, ethofumesate, etobenzanid, endothal disodium, oxadiazon, oxadiargyl, oxaziclomefone, oxasulfuron, oxyfluorfen, oryzalin, orthosulfamuron, orthobencarb, oleic acid, carfentrazone-ethyl, carbetamide, quizalofop-P-ethyl, quinoclamine, quinclorac, quinmerac, cumyluron, clethodim, clodinafop-propargyl, clopyralid, clomazone, chlomethoxyfen, clomeprop, cloransulam-methyl, chloramben, chlorimuron-ethyl, DCBN, chlorphthalim, chloroxuron, chlorsulfuron, chlornitrofen, chlorbufam, chlorflurenol-methyl, chlorpropham, chlorbromuron, chlorotoluron, chloroacetic acid, *Xanthomonas campestris*, cyanazine, sodium cyanate, cycloate, cycloxydim, diclosulam, cyclosulfamuron, dichlorprop, DBN, diclofop-methyl, diquat-dibromide, dithiopyr, siduron, dinitramine, cinidon-ethyl, cinosulfuron, dinoseb, dinoterb, cyhalofop-butyl, difenoxuron, difenzoquat, diflufenican, diflufenzopyr, dipropetryn, dimethametryn, simetryne, dimepiperate, dimefuron, simazine, cinmethylin, sulcotrione, sulfentrazone, sulfosulfuron, sulfometuron-methyl, sethoxydim, terbacil, terbuthylazine, terbutryne, dymron, dazomet, terbumeton, dalapon, thiazafluron, thiazopyr, thiencarbazone, tiocarbazil, thidiazimin, thifensulfuron-methyl, desmedipham, tetrapion, tebutam, tebuthiuron, tepraloxydim, tefuryltrione, desmetryne, tembotrione, topramezone, tralkoxydim, triaziflam, triasulfuron, tri-allate, trietazine, triclopyr, tritosulfuron, triofensulfuron, triflusulfuron-methyl, trifluralin, trifloxysulfuron-sodium, tribenuron-methyl, Drechsrela monoceras, naptalam, nicosulfuron, neburon, norflurazon, paraquat-dichloride, haloxyfop, halosafen, halosulfuron-methyl, bialaphos, picloram, picolinafen, bispyribac-sodium, pinoxaden, bifenox, pyrachlonil, pyrasulfotole, pyrazoxyfen, pyrazosulfuron-ethyl, pyrazolate, pyrazon, pyraflulfen-ethyl, pyridafol, pyrithiobac-sodium, pyridate, pyriftalid, pyributicarb, pyribenzoxim, pyrimisulfan, pyriminobac-methyl, pyroxasulfone, pyroxsulam, prometryne, fenuron, fenoxasulfone, fenoxaprop-P-ethyl, phenmedipham, fosamine-ammonium, fomesafen, foramsulfuron, butafenacil, butamiphos, butylate, butralin, butroxydim, flumetsulam, flazasulfuron, flamprop, primisulfuron-methyl, fluazifop, fluazolate, fluometuron, fluoroglycofen-ethyl, flucarbazone-sodium, fluchloralin, flucetosulfuron, fluthiacet-methyl, flupyrsulfuron-methyl-sodium, flufenpyr-ethyl, flupoxam, flumioxazin, flumiclorac-pentyl, fluridone, flurenol, proglinazine-ethyl, prodiamine, prosulfuron, propaquizofop, propazine, propanil, propyzamide, propyrisulfuron, propham, profoxydim, profluazol, prosulfocarb, propoxycarbazone-sodium, bromacil, prometon, bromoxynil, bromofenoxim, bromobutide, florasulam, fluroxypyr, flurochloridone, flurtamone, hexazinone, benazolin-ethyl, benefin, penoxsulam, beflubutamid, pebulate, pelargonic acid, vernolate, bencarbazone), benzfendizone, bensulide, bensulfuron-methyl, benzobicyclon, benzofenap, bentazon, pentanochlor, benthiocarb, pendimethalin, pentoxazone, benfuresate, mesosulfuron-methyl, mesotrione, methasulfocarb, methabenzthiazuron, metamitron, metamifop, metazosulfuron, metam, MSMA (methylarsonic acid), methiozolin, methyldymron, metoxuron, metosulam, metsulfuron-methyl, methoprotryne, metobromuron, metobenzuron, metribuzin, monosulfuron, monolinuron, molinate, iodosulfuron-methyl-sodium, lactofen, linuron, rimsulfuron, lenacil, DCMU (Diuron), sodium chlorate, 2,3,6-TBA(2,3,6-trichlorobenzoic acid), 2,4,5-T(2,4,5-trichlorophenoxyacetic acid), 2,4-DB(4-(2,4-dichlorophenoxy)butyric acid), 2,4-PA (2,4-Dichlorophenoxyacetic acid), DNOC(4,6-dinitro-O-cresol), EPIC (S-ethyl dipropylthiocarbamate), MCPA((4-chloro-2-methylphenoxy)acetic acid), MCPB(4-(4-chloro-2-methylphenoxy)butryric acid), MDBA (dicamba), sodium-trichloroacetate, hexanoic acid, heptanoic acid, octanoic acid, decanoic acid, undecanoic acid, dodecanoic acid, trimethyl hexanoic acid, cedar essence oil, cedarwood oil, Japanese cypress oil, eucalyptus oil, clove oil, citrus oil and lemon oil.

Further, the inhibitor for tobacco auxiliary bud growth of the present invention may further contain other insecticides, bactericides, plant growth regulators, fertilizers and the like to expand the range of action.

EXAMPLES

Examples of the present inventions are described hereinafter.

Formulation examples are given first. The active ingredients, kinds of the additives and the compounding ratio thereof are not limited to the description set forth below and may be varied over a wide range. Here, the term "part(s)" means "part(s) by mass" in the following examples.

Formulation Example 1

An emulsion was obtained by dissolving 10 parts by mass of Cafenstrole (manufactured by SDS BIOTECK K. K.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 2

An emulsion was obtained by dissolving 10 parts by mass of Thenylchlor (manufactured by SDS BIOTECH K. K.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 3

An emulsion was obtained by dissolving 10 parts by mass of alachlor (manufactured by Wako Pure Chemical Industries, Ltd.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 4

An emulsion was obtained by dissolving 10 parts by mass of butachlor (manufactured by Wako Pure Chemical Industries, Ltd.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 5

An emulsion was obtained by dissolving 10 parts by mass of metolachlor (manufactured by Wako Pure Chemical Industries, Ltd.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 6

An emulsion was obtained by dissolving 10 parts by mass of pletilachlor (manufactured by Wako Pure Chemical Industries, Ltd.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 7

An emulsion was obtained by dissolving 10 parts by mass of dimethenamid (manufactured by Wako Pure Chemical Industries, Ltd.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 8

A flowable formulation was obtained by mixing well 10 parts by mass of fentrazamide (manufactured by Wako Pure Chemical Industries, Ltd.), 11 parts by mass of propylene glycol, 3 parts by mass of Sorpol 7290P (tradename; manufactured by TOHO CHEMICAL INDUSTRY Co., Ltd.), 0.1 part by mass of Toxanon N100 (tradename; manufactured by Sanyo Chemical Industries, Ltd.), 0.2 parts by mass of Antifoam E-20 (tradename; manufactured by KAO Corporation), 1.5 parts by mass of Kunipia F (tradename; manufactured by Kunimine Industries Co., Ltd.) and 74.2 parts by mass of water; and pulverizing the mixture by a wet method till the particle size becomes 5 μm or less.

Formulation Example 9

A flowable formulation was obtained by mixing well 10 parts by mass of Indanofan (manufactured by Wako Pure Chemical Industries, Ltd.), 11 parts by mass of propylene glycol, 3 parts by mass of Sorpol 7290P (tradename; manufactured by TOHO CHEMICAL INDUSTRY Co., Ltd.), 0.1 part by mass of Toxanon N100 (tradename; manufactured by Sanyo Chemical Industries, Ltd.), 0.2 parts by mass of Antifoam E-20 (tradename; manufactured by KAO Corporation), 1.5 parts by mass of Kunipia (tradename; manufactured by Kunimine Industries Co., Ltd.) and 74.2 parts by mass of water; and pulverizing the mixture by a wet method till the particle size becomes 5 μm or less.

Formulation Example 10

An emulsion was obtained by dissolving 10 parts by mass of propisochlor (manufactured by Sigma-Aldrich Japan) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 11

A flowable formulation was obtained by mixing well 10 parts by mass of Cafenstrole (manufactured by SDS BIOTECK K. K.), 11 parts by mass of propylene glycol, 3 parts by mass of Sorpol 7290P (tradename; manufactured by TOHO CHEMICAL INDUSTRY Co., Ltd.), 0.1 part by mass of Toxanon N100 (tradename; manufactured by Sanyo Chemical Industries, Ltd.), 0.2 parts by mass of Antifoam E-20 (tradename; manufactured by KAO Corporation), 1.5 parts by mass of Kunipia (tradename; manufactured by Kunimine Industries Co., Ltd.) and 74.2 parts by mass of water; and pulverizing the mixture by a wet method till the particle size becomes 5 µm or less.

Formulation Example 12

A flowable formulation was obtained by mixing well 10 parts by mass of Thenylchlor (manufactured by SDS BIO-TECK K. K.), 11 parts by mass of propylene glycol, 3 parts by mass of Sorpol 7290P (tradename; manufactured by TOHO CHEMICAL INDUSTRY Co., Ltd.), 0.1 part by mass of Toxanon N100 (tradename; manufactured by Sanyo Chemical Industries, Ltd.), 0.2 parts by mass of Antifoam E-20 (tradename; manufactured by KAO Corporation), 1.5 parts by mass of Kunipia (tradename; manufactured by Kunimine Industries Co., Ltd.) and 74.2 parts by mass of water; and pulverizing the mixture by a wet method till the particle size becomes 5 µm or less.

Formulation Example 13

A flowable formulation was obtained by mixing well 10 parts by mass of chlorthal-dimethyl (manufactured by SDS BIOTECK K. K.), 11 parts by mass of propylene glycol, 3 parts by mass of Sorpol 7290P (tradename; manufactured by TOHO CHEMICAL INDUSTRY Co., Ltd.), 0.1 part by mass of Toxanon N100 (tradename; manufactured by Sanyo Chemical Industries, Ltd.), 0.2 parts by mass of Antifoam E-20 (tradename; manufactured by KAO Corporation), 1.5 parts by mass of Kunipia (tradename; manufactured by Kunimine Industries Co., Ltd.) and 74.2 parts by mass of water; and pulverizing the mixture by a wet method till the particle size becomes 5 µm or less.

Next, Test Examples are described below, which tests were conducted to confirm the efficacy of the inhibitor for tobacco auxiliary bud growth of the present invention.

Test Example 1

Tobacco seedlings of Tsukuba 1 (flue-cured cultivar) and Michinoku 1 (burley cultivar) were transplanted to 1/5000a Wagner pots filled with Kureha garden nursery soil. The plants were grown in a glasshouse, and the floral axis parts were removed at the time of single-flower bloom of tobacco (top pruning).

The formulations of the inhibitors for tobacco axillary bud growth obtained in Formulation Examples 1 to 10 above were each diluted with water to predetermined concentrations, and 20 ml of the water-diluted solutions of the respective inhibitors were separately sprayed using a contact-type axillary bud inhibitor spraying instrument equipped with a spot exhaust nozzle (Examples 1 to 11 and 12 to 22). In addition, butralin (trade name: Blue Ribbon) (Comparative Examples 1 and 3) and decyl alcohol (trade name: Contact) (Comparative Examples 2 and 4) were used for tests as comparative examples in the same manner as above. In the cases of both the flue-cured cultivar and burley cultivar, one plant was planted per pot, and the tests were carried out in duplicate.

For the respective cases, states of inhibition of axillary bud growth 28 days after the spraying were investigated together with untreated groups sprayed with no inhibitor, and axillary bud growth inhibition ratios were calculated by the following equation.

Axillary bud growth inhibition ratio=(fresh weight of axillary buds per plant of untreated group−fresh weight of axillary buds per plant of treated group)÷(fresh weight of axillary buds per plant of untreated group)×100    [Math. 1]

Further, the presence or absence of the harmful effect of each inhibitor was evaluated in one of the following four categories depending on the degrees of growth inhibition, gangrene, change in color, deformation and the like of leaves (first to fourth leaves from the top).

Large: A severely harmful effect was observed.
Middle: A clearly harmful effect was observed.
Small: A slightly harmful effect was observed.
Absent: No harmful effect was observed.

For each of the examples, the axillary bud growth inhibition ratio and the presence or absence of the harmful effects of the inhibitor are shown in Table 1 (flue-cured cultivar) and Table 2 (burley cultivar).

TABLE 1

| | Test compound | Concentration of active ingredient (%) | Axillary bud growth inhibition ratio (%) | Harmful effect of inhibitor |
|---|---|---|---|---|
| Example 1 | Cafenstrole (Formulation Example 1) | 0.1 | 100 | Absent |
| Example 2 | Thenylchlor (Formulation Example 2) | 0.1 | 96 | Absent |
| Example 3 | Alachlor (Formulation Example 3) | 0.1 | 97 | Absent |
| Example 4 | Butachlor (Formulation Example 4) | 0.1 | 100 | Absent |
| Example 5 | Metolachlor (Formulation Example 5) | 0.1 | 95 | Absent |
| Example 6 | Pretilachlor (Formulation Example 6) | 0.1 | 93 | Absent |
| Example 7 | Dimethenamid (Formulation Example 7) | 0.1 | 92 | Absent |
| Example 8 | Fentrazamide (Formulation Example 8) | 0.1 | 94 | Absent |
| Example 9 | Indanofan (Formulation Example 9) | 0.1 | 100 | Absent |
| Example 10 | Propisochlor (Formulation Example 10) | 0.1 | 86 | Absent |
| Example 11 | Propisochlor (Formulation Example 10) | 0.2 | 98 | Absent |
| Comparative Example 1 | Butralin | 0.35 | 98 | Small |
| Comparative Example 2 | Decyl alcohol | 2.6 | 91 | Small |

TABLE 2

|  | Test compound | Concentration of active ingredient (%) | Axillary bud growth inhibition ratio (%) | Harmful effect of inhibitor |
|---|---|---|---|---|
| Example 12 | Cafenstrole (Formulation Example 1) | 0.1 | 99 | Absent |
| Example 13 | Thenylchlor (Formulation Example 2) | 0.1 | 95 | Absent |
| Example 14 | Alachlor (Formulation Example 3) | 0.1 | 91 | Absent |
| Example 15 | Butachlor (Formulation Example 4) | 0.1 | 96 | Absent |
| Example 16 | Metolachlor (Formulation Example 5) | 0.1 | 91 | Absent |
| Example 17 | Pretilachlor (Formulation Example 6) | 0.1 | 92 | Absent |
| Example 18 | Dimethenamid (Formulation Example 7) | 0.1 | 94 | Absent |
| Example 19 | Fentrazamide (Formulation Example 8) | 0.1 | 92 | Absent |
| Example 20 | Indanofan (Formulation Example 9) | 0.1 | 95 | Absent |
| Example 21 | Propisochlor (Formulation Example 10) | 0.1 | 84 | Absent |
| Example 22 | Propisochlor (Formulation Example 10) | 0.2 | 95 | Absent |
| Comparative Example 3 | Butralin | 0.35 | 96 | Small |
| Comparative Example 4 | Decyl alcohol | 2.6 | 92 | Small |

Test Example 2

The formulation of Formulation Example 1 (cafenstrole), Formulation Example 2 (thenylchlor) or Formulation Example 10 (propisochlor) above was diluted with water to predetermined concentrations and mixed with decyl alcohol (manufactured by Wako Pure Chemical Industries, Ltd.), 2-ethylhexanol (manufactured by Wako Pure Chemical Industries, Ltd.) or geraniol (manufactured by Wako Pure Chemical Industries, Ltd.) at predetermined concentrations, and the resultant was adjusted and used for tests (Examples 23 to 31 and 32 to 40). In addition, as comparative examples, the formulation of Formulation Example 1, Formulation Example 3, or Formulation Example 10 diluted with water to predetermined concentrations (Comparative Examples 5 to 7 and 11 to 13) and decyl alcohol, 2-ethylhexanol or geraniol diluted with water to a predetermined concentration were used for tests (Comparative Examples 8 to 10 and 14 to 16).

The respective inhibitors were sprayed in the same manner as in Test Example 1, and states of inhibition of axillary bud growth 28 days after the spraying were investigated together with untreated groups sprayed with no inhibitor. Then, axillary bud growth inhibition ratios were calculated.

The results are shown in Table 3 (flue-cured cultivar) and Table 4 (burley cultivar).

TABLE 3

|  | Test compound | Concentration of active ingredient (%) | Axillary bud growth inhibition ratio (%) |
|---|---|---|---|
| Example 23 | Cafenstrole + decyl alcohol | 0.05 + 0.5 | 100 (86) |
| Example 24 | Cafenstrole + 2-ethylhexanol | 0.05 + 0.5 | 98 (81) |
| Example 25 | Cafenstrole + geraniol | 0.05 + 0.5 | 100 (83) |
| Example 26 | Thenylchlor + decyl alcohol | 0.05 + 0.5 | 100 (85) |
| Example 27 | Thenylchlor + 2-ethylhexanol | 0.05 + 0.5 | 97 (80) |
| Example 28 | Thenylchlor + geraniol | 0.05 + 0.5 | 98 (82) |
| Example 29 | Propisochlor + decyl alcohol | 0.1 + 0.5 | 100 (92) |
| Example 30 | Propisochlor + 2-ethylhexanol | 0.1 + 0.5 | 98 (89) |
| Example 31 | Propisochlor + geraniol | 0.1 + 0.5 | 100 (90.2) |
| Comparative Example 5 | Cafenstrole | 0.05 | 76 |
| Comparative Example 6 | Thenylchlor | 0.05 | 74 |
| Comparative Example 7 | Propisochlor | 0.1 | 86 |
| Comparative Example 8 | Decyl alcohol | 0.5 | 42 |
| Comparative Example 9 | 2-Ethylhexanol | 0.5 | 21 |
| Comparative Example 10 | Geraniol | 0.5 | 30 |

TABLE 4

|  | Test compound | Concentration of active ingredient (%) | Axillary bud growth inhibition ratio (%) |
|---|---|---|---|
| Example 32 | Cafenstrole + decyl alcohol | 0.05 + 0.5 | 100 (85) |
| Example 33 | Cafenstrole + 2-ethylhexanol | 0.05 + 0.5 | 100 (82) |
| Example 34 | Cafenstrole + geraniol | 0.05 + 0.5 | 99 (80) |
| Example 35 | Thenylchlor + decyl alcohol | 0.05 + 0.5 | 95 (84) |
| Example 36 | Thenylchlor + 2-ethylhexanol | 0.05 + 0.5 | 96 (80) |
| Example 37 | Thenylchlor + geraniol | 0.05 + 0.5 | 98 (78) |
| Example 38 | Propisochlor + decyl alcohol | 0.1 + 0.5 | 100 (91) |

TABLE 4-continued

| | Test compound | Concentration of active ingredient (%) | Axillary bud growth inhibition ratio (%) |
|---|---|---|---|
| Example 39 | Propisochlor + 2-ethylhexanol | 0.1 + 0.5 | 98 (89) |
| Example 40 | Propisochlor + geraniol | 0.1 + 0.5 | 99 (88) |
| Comparative Example 11 | Cafenstrole | 0.05 | 72 |
| Comparative Example 12 | Thenylchlor | 0.05 | 70 |
| Comparative Example 13 | Propisochlor | 0.1 | 83 |
| Comparative Example 14 | Decyl alcohol | 0.5 | 46 |
| Comparative Example 15 | 2-Ethylhexanol | 0.5 | 34 |
| Comparative Example 16 | Geraniol | 0.5 | 28 |

Test Example 3

The formulation of Formulation Example 11 (cafenstrole), Formulation Example 12 (thenylchlor) or Formulation Example 13 (chlorthal-dimethyl) above was diluted with water to predetermined concentrations, and the resultant was mixed, adjusted and used for tests (Examples 41 to 58 and 59 to 76). In addition, as comparative examples, the formulation of Formulation Example 11, Formulation Example 12 or Formulation Example 13 diluted with water to predetermined concentrations (Comparative Examples 21 to 29 and 34 to 42), butralin (trade name: Blue Ribbon) (Comparative Examples 17, 18, 30, and 31) and decyl alcohol (trade name: Contact) (Comparative Examples 19, 20, 32, and 33) were used for tests in the same manner as above.

The respective inhibitors were sprayed in the same manner as in Test Example 1, and states of inhibition of axillary bud growth 28 days after the spraying were investigated together with untreated groups sprayed with no inhibitor. Then, axillary bud growth inhibition ratios were calculated.

The results are shown in Table 5 (flue-cured cultivar) and Table 6 (burley cultivar).

TABLE 5

| | Test compound | Concentration of active ingredient (%) | Axillary bud growth inhibition ratio (%) | Harmful effect of inhibitor |
|---|---|---|---|---|
| Example 41 | Cafenstrole + chlorthal-dimethyl | 0.002 + 0.05 | 88 (53) | Absent |
| Example 42 | Cafenstrole + chlorthal-dimethyl | 0.002 + 0.1 | 98 (82) | Absent |
| Example 43 | Cafenstrole + chlorthal-dimethyl | 0.002 + 0.2 | 99 (90) | Absent |
| Example 44 | Cafenstrole + chlorthal-dimethyl | 0.005 + 0.05 | 92 (54) | Absent |
| Example 45 | Cafenstrole + chlorthal-dimethyl | 0.005 + 0.1 | 99 (82) | Absent |
| Example 46 | Cafenstrole + chlorthal-dimethyl | 0.005 + 0.2 | 100 (90) | Absent |
| Example 47 | Cafenstrole + chlorthal-dimethyl | 0.01 + 0.05 | 99 (56) | Absent |
| Example 48 | Cafenstrole + chlorthal-dimethyl | 0.01 + 0.1 | 100 (83) | Absent |
| Example 49 | Cafenstrole + chlorthal-dimethyl | 0.01 + 0.2 | 100 (91) | Absent |
| Example 50 | Thenylchlor + chlorthal-dimethyl | 0.002 + 0.05 | 85 (50) | Absent |
| Example 51 | Thenylchlor + chlorthal-dimethyl | 0.002 + 0.1 | 92 (81) | Absent |
| Example 52 | Thenylchlor + chlorthal-dimethyl | 0.002 + 0.2 | 98 (89) | Absent |
| Example 53 | Thenylchlor + chlorthal-dimethyl | 0.005 + 0.05 | 94 (51) | Absent |
| Example 54 | Thenylchlor + chlorthal-dimethyl | 0.005 + 0.1 | 98 (81) | Absent |
| Example 55 | Thenylchlor + chlorthal-dimethyl | 0.005 + 0.2 | 100 (90) | Absent |
| Example 56 | Thenylchlor + chlorthal-dimethyl | 0.01 + 0.05 | 99 (56) | Absent |
| Example 57 | Thenylchlor + chlorthal-dimethyl | 0.01 + 0.1 | 100 (83) | Absent |
| Example 58 | Thenylchlor + chlorthal-dimethyl | 0.01 + 0.2 | 100 (91) | Absent |
| Comparative Example 17 | Butralin | 0.03 | 44 | Absent |
| Comparative Example 18 | Butralin | 0.35 | 98 | Small |
| Comparative Example 19 | Decyl alcohol | 0.03 | 0 | Absent |
| Comparative Example 20 | Decyl alcohol | 2.6 | 91 | Middle |
| Comparative Example 21 | Cafenstrole | 0.002 | 17 | Absent |
| Comparative Example 22 | Cafenstrole | 0.005 | 20 | Absent |
| Comparative Example 23 | Cafenstrole | 0.01 | 23 | Absent |
| Comparative Example 24 | Thenylchlor | 0.002 | 12 | Absent |
| Comparative Example 25 | Thenylchlor | 0.005 | 14 | Absent |
| Comparative Example 26 | Thenylchlor | 0.01 | 22 | Absent |
| Comparative Example 27 | Chlorthal-dimethyl | 0.05 | 43 | Absent |
| Comparative Example 28 | Chlorthal-dimethyl | 0.1 | 78 | Absent |

TABLE 5-continued

| | Test compound | Concentration of active ingredient (%) | Axillary bud growth inhibition ratio (%) | Harmful effect of inhibitor |
|---|---|---|---|---|
| Comparative Example 29 | Chlorthal-dimethyl | 0.2 | 88 | Absent |

TABLE 6

| | Test compound | Concentration of active ingredient (%) | Axillary bud growth inhibition ratio (%) | Harmful effect of inhibitor |
|---|---|---|---|---|
| Example 59 | Cafenstrole + chlorthal-dimethyl | 0.002 + 0.05 | 90 (48) | Absent |
| Example 60 | Cafenstrole + chlorthal-dimethyl | 0.002 + 0.1 | 95 (75) | Absent |
| Example 61 | Cafenstrole + chlorthal-dimethyl | 0.002 + 0.2 | 100 (85) | Absent |
| Example 62 | Cafenstrole + chlorthal-dimethyl | 0.005 + 0.05 | 94 (51) | Absent |
| Example 63 | Cafenstrole + chlorthal-dimethyl | 0.005 + 0.1 | 100 (77) | Absent |
| Example 64 | Cafenstrole + chlorthal-dimethyl | 0.005 + 0.2 | 100 (85) | Absent |
| Example 65 | Cafenstrole + chlorthal-dimethyl | 0.01 + 0.05 | 100 (54) | Absent |
| Example 66 | Cafenstrole + chlorthal-dimethyl | 0.01 + 0.1 | 100 (78) | Absent |
| Example 67 | Cafenstrole + chlorthal-dimethyl | 0.01 + 0.2 | 100 (87) | Absent |
| Example 68 | Thenylchlor + chlorthal-dimethyl | 0.002 + 0.05 | 88 (46) | Absent |
| Example 69 | Thenylchlor + chlorthal-dimethyl | 0.002 + 0.1 | 96 (74) | Absent |
| Example 70 | Thenylchlor + chlorthal-dimethyl | 0.002 + 0.2 | 100 (84) | Absent |
| Example 71 | Thenylchlor + chlorthal-dimethyl | 0.005 + 0.05 | 92 (52) | Absent |
| Example 72 | Thenylchlor + chlorthal-dimethyl | 0.005 + 0.1 | 99 (77) | Absent |
| Example 73 | Thenylchlor + chlorthal-dimethyl | 0.005 + 0.2 | 100 (86) | Absent |
| Example 74 | Thenylchlor + chlorthal-dimethyl | 0.01 + 0.05 | 100 (56) | Absent |
| Example 75 | Thenylchlor + chlorthal-dimethyl | 0.01 + 0.1 | 100 (79) | Absent |
| Example 76 | Thenylchlor + chlorthal-dimethyl | 0.01 + 0.2 | 100 (87) | Absent |
| Comparative Example 30 | Butralin | 0.03 | 48 | Absent |
| Comparative Example 31 | Butralin | 0.35 | 97 | Small |
| Comparative Example 32 | Decyl alcohol | 0.03 | 0 | Absent |
| Comparative Example 33 | Decyl alcohol | 2.6 | 94 | Small |
| Comparative Example 34 | Cafenstrole | 0.002 | 15 | Absent |
| Comparative Example 35 | Cafenstrole | 0.005 | 19 | Absent |
| Comparative Example 36 | Cafenstrole | 0.01 | 25 | Absent |
| Comparative Example 37 | Thenylchlor | 0.002 | 11 | Absent |
| Comparative Example 38 | Thenylchlor | 0.005 | 22 | Absent |
| Comparative Example 39 | Thenylchlor | 0.01 | 28 | Absent |
| Comparative Example 40 | Chlorthal-dimethyl | 0.05 | 39 | Absent |
| Comparative Example 41 | Chlorthal-dimethyl | 0.1 | 71 | Absent |
| Comparative Example 42 | Chlorthal-dimethyl | 0.2 | 82 | Absent |

It should be noted that the values in parentheses in Tables 3 to 6 represent predicted values of the effects of inhibiting axillary bud growth of mixed agents (that is, compounds mixed as active ingredients), that is, expected values of additive effects. The expected values were calculated by the following Colby's equation (Colby. S. R.; "Calculating Synergistic and Antagonistic Responses of Herbicide Combinations" Weed, Vol. 15(1), 20-22, 1967).

Colby's equation: $E = x + y - x \cdot y / 100$ [Math. 2]

E: Axillary bud growth inhibition ratio in the case of using a mixture of active compound A (concentration a) and active compound B (concentration b) (theoretical axillary bud growth inhibition ratio)

x: Axillary bud growth inhibition ratio in the case of using active compound A at concentration a y: Axillary bud growth inhibition ratio in the case of using active compound B at concentration b In the case where a measured value determined in the above-mentioned test (axillary bud growth inhibition ratio)

was larger than the expected value, a synergetic effect was expressed on activity to suppress axillary bud growth.

As shown in Tables 1 and 2, the inhibitors for tobacco axillary bud growth of the present invention exhibited inhibition ratios as high as 90% or more for each of the flue-cured cultivar and the burley cultivar, at lower concentrations than those of the control compounds. Further, all the inhibitors for tobacco axillary bud growth of the present invention exhibited no harmful effect (Examples 1 to 22).

In addition, as shown in Tables 3 and 4, all the measured values of the inhibitors for tobacco axillary bud growth including the aliphatic alcohol in combination (Examples 23 to 40) are larger than the expected values of the additive effects determined from the measured values of the agents including only one component (Comparative Examples 5 to 16), which shows that the inhibitors have synergistic effects.

As shown in Tables 5 and 6, the measured values of the inhibitors for tobacco axillary bud growth of the present invention including cafenstrole and chlorthal-dimethyl in combination (Examples 41 to 49 and 59 to 67) or the inhibitors for tobacco axillary bud growth of the present invention including thenylchlor and chlorthal-dimethyl in combination (Examples 50 to 58 and 68 to 76) are larger than the expected values due to the additive effects determined from the measured values of the agents including a single component (Comparative Examples 21 to 29 and 34 to 42) for each of the flue-cured cultivar and the burley cultivar, which shows that the inhibitors have synergistic effects. The inhibitors for tobacco axillary bud growth of the present invention exhibited higher inhibition ratios at lower concentrations than those of the control compounds (Comparative Examples 17 to 20 and 30 to 33). Further, all the inhibitors for tobacco axillary bud growth of the present invention exhibited no harmful effect (Examples 41 to 76).

As apparent from the above, the inhibitor for tobacco axillary bud growth of the present invention has high effects of inhibiting axillary bud growth as compared to existing inhibitors for tobacco axillary bud growth and is excellent in terms of sustained chemical efficacy. In addition, it has been proved that the inhibitor for tobacco axillary bud growth of the present invention is superior also from the standpoint of causing no harmful effect.

The invention claimed is:

1. An inhibitor for tobacco axillary bud growth, comprising, as an active ingredient,
one or more very-long chain fatty acid synthesis inhibitors selected from the group consisting of a chloroacetamide-based compound, an oxyacetamide-based compound, an alkanamide-based compound, fentrazamide, cafenstrole, anilofos, piperophos, indanofan, ipfencarbazone, tridiphane and epronaz.

2. The inhibitor for tobacco axillary bud growth according to claim 1, in which the very-long chain fatty acid synthesis inhibitors comprise one or more compounds selected from the group consisting of a chloroacetamide-based compound, fentrazamide, cafenstrole and indanofan.

3. The inhibitor for tobacco axillary bud growth according to claim 2, comprising, as an active ingredient, a chloroacetamide-based compound selected from the group consisting of thenylchlor, metolachlor, alachlor, dimethenamid, butachlor, pretilachlor and propisochlor.

4. The inhibitor for tobacco axillary bud growth according to claim 1, further including chlorthal-dimethyl.

5. The inhibitor for tobacco axillary bud growth according to claim 4, comprising cafenstrole or thenylchlor; and chlorthal-dimethyl.

6. The inhibitor for tobacco axillary bud growth according to claim 1, further comprising decyl alcohol, 2-ethyl hexanol, or geraniol.

7. A method for inhibiting tobacco axillary bud growth, comprising applying to a tobacco plant the inhibitor for tobacco axillary bud growth according to claim 1.

8. The inhibitor for tobacco axillary bud growth according to claim 1, comprising, as an active ingredient, an oxyacetamide-based compound selected from the group consisting of flufenacet and mefenacet.

9. The inhibitor for tobacco axillary bud growth according to claim 1, comprising, as an active ingredient, an alkanamide-based compound selected from the group consisting of diphenamid, naproanilide and napropamide.

10. The method according to claim 7, comprising, as an active ingredient, a chloroacetamide-based compound selected from the group consisting of thenylchlor, metolachlor, alachlor, dimethenamid, butachlor, pretilachlor and propisochlor.

11. The method according to claim 7, wherein the inhibitor further comprises chlorthal-dimethyl.

12. The method according to claim 11, wherein the inhibitor comprises cafenstrole or thenylchlor; and chlorthal-dimethyl.

13. The method according to claim 7, wherein the inhibitor further comprises decyl alcohol, 2-ethyl hexanol, or geraniol.

* * * * *